United States Patent [19]

Kawamonzen et al.

[11] Patent Number: 5,403,936

[45] Date of Patent: Apr. 4, 1995

[54] ORGANIC NONLINEAR OPTICAL MATERIAL AND NONLINEAR OPTICAL ELEMENT

[75] Inventors: Yoshiaki Kawamonzen, Yokohama; Yasushi Mori, Tokyo, both of Japan

[73] Assignee: Kabushiki Kaisha Toshiba, Kawasaki, Japan

[21] Appl. No.: 854,755

[22] Filed: Mar. 20, 1992

Related U.S. Application Data

[63] Continuation of Ser. No. 594,120, Oct. 9, 1990, abandoned.

[30] Foreign Application Priority Data

Oct. 9, 1989 [JP] Japan .................. 1-262052
Mar. 27, 1990 [JP] Japan .................. 2-75412

[51] Int. Cl.⁶ ............... C07D 263/08; C07C 143/68
[52] U.S. Cl. .............................................. 548/228
[58] Field of Search .................. 359/326, 328, 329; 548/228

[56] References Cited

U.S. PATENT DOCUMENTS 4,727,155 2/1988 Kuhn ................................. 548/228

FOREIGN PATENT DOCUMENTS 0335641 10/1988 European Pat. Off. .
3707835 9/1987 Germany .
2083239 3/1982 United Kingdom .

OTHER PUBLICATIONS

Organic Reactions, vol. 3, Chap. 5, H. E. Carter (1946), "Azlactones", pp. 198–239.
Miguchi et al, "Organic Non-linear Optical material", JP03050532A2 and JP89-186281 (19 Jul. 1989), Abstract only.
CA 98(22):188999h. Horic et al "Electrophotographic Light-sensitive material" *Germ. Offen.*, 56 pp. 5 Jan. 1983. Corresponds to DE3222024A1.
Kurihara et al, CA110(4):250769, "Nonlinear organic optical materials" *Jpn. Kokai Tokkyo Koho*, 6 pp. Jan. 1988. Corresponding to [JP-63175838-A2.].
Almirante, et al, "Reactions of 1-aryl-4,5-dihydro-4-methylene-5-morpholino-v-triazoles with 2,4-diaryl-5 (4H)-oxazolones", Jul. 20, 1987, pp. 1073–1078.

Primary Examiner—Raymond Henley, III
Assistant Examiner—Keith MacMillan
Attorney, Agent, or Firm—Oblon, Spivak, McClelland, Maier & Neustadt

[57] ABSTRACT

Disclosed is an organic nonlinear optical material made of heterocyclic compound which is represented by general formula (I) shown below.

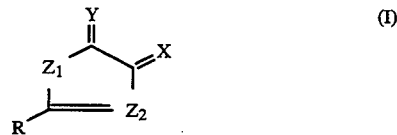

wherein $Z_1$ is O, S, Se, Te, $SO_2$ group or $NR_1$ group; $Z_2$ is N or $CR_2$ group; Y is O, S or $NR_3$ group; X is $CR_4R_5$ group, $NR_6$ group, O or S; and R, $R_1$, $R_2$, $R_3$, $R_4$, $R_5$, and $R_6$ may be identical to or different from each other, and each of them is heterocyclic group, aromatic hydrocarbon group, aliphatic hydrocarbon group or alicyclic hydrocarbon group, which may be unsubstituted or substituted, characteristic group or H, where $R_4$ and $R_5$ may jointly form a carbocyclic or a heterocyclic ring.

15 Claims, 1 Drawing Sheet

ORGANIC NONLINEAR OPTICAL MATERIAL AND NONLINEAR OPTICAL ELEMENT

This application is a continuation of application Ser. No. 07/594,120, filed Oct. 9, 1990, now abandoned.

BACKGROUND OF THE INVENTION

1. Field of the Invention

The present invention relates to a novel organic nonlinear optical material and a nonlinear optical element having this organic nonlinear optical material which generates short wavelength light by conversion of a laser beam into a second harmonic wave.

2. Description of the Related Art

Light communication and light information processing are expected as basic technologies for the development of information in future. It is essential for these technologies to establish means for properly controlling the wavelength, the amplitude, and phases of laser beams, in other words harmonic generation, light switching, and light mixing are important aspects of nonlinear optical material. The utilization of the nonlinear optical effect is quite advantageous in controlling the properties of light at fast speeds.

Conventionally, inorganic ferroelectric crystals, for example bulk crystals made of $LiNbO_3$ and KTP, are used for the conversion of light of wave lengths of YAG lasers and dye lasers. However, these inorganic materials cannot sufficiently yield the desired nonlinear optical effect. Because of this reason, they are merely used for high-output lasers, but they are used in to low-output semiconductor lasers which have been developed in recent years.

On the other hand, recently, a variety of organic compounds have been found, which have a far greater nonlinear optical constant than that of inorganic crystals and excellent durability against optical damage. It is expected that the utilization of these organic nonlinear optical materials will lead to elements which are capable of generating a sufficient second harmonic wave for low-output semiconductor lasers.

There are a number of technical papers which discuss organic nonlinear optical materials including the following: "Nonlinear Optical Properties of Organic and Polymeric Materials", by D. J. Williams et al., published by American Chemical Society, in 1983, and "Nonlinear Optical properties of Organic Molecules and Crystals", by D. S. Chelma and J. Zyss, published by Academic Press, in 1987, for example.

The feature of the molecular structure of such organic nonlinear optical materials is that an electron-releasing group and an electron-withdrawing group are attached to a $\pi$-electron system like the benzene ring at opposite positions from each other.

However, the dipole moment in the ground state inevitably increases in these organic nonlinear optical materials having the above-mentioned molecular structure. In a solid made of molecules having a large dipole moment, energetic stability is obtained when the molecules are aligned with their dipole moments in opposite directions to each other, and thus the molecules are likely to be crystallized in the form of centrosymmetry. With regard to the centrosymmetric crystals, second harmonic generation is inhibited in principle. The nonlinear characteristic is promoted in such molecules which have wide spread $\pi$-electron systems. On the other hand, the absorption band of the molecules superposes the wavelength of the fundamental wave or the second harmonic wave and retards effective second harmonic generation.

Furthermore, as in the case of using an inorganic compound, if a nonlinear optical element is manufactured by using a bulk crystal made of organic nonlinear optical material, some problems are encountered as described below. First, in order to produce bulk crystals made of organic nonlinear optical materials, those processes rarely applicable to organic materials must be executed, which include growth, cutting, and polishing of single-crystals. Crystals of organic compounds are in general molecular crystals containing weakly bonded molecules, in other words, have weaker mechanical strength than those of inorganic crystals, and thus much difficulty is involved in the execution of the above-mentioned processes.

Furthermore, when operating the wavelength converting element composed of bulk crystals, it is essential to achieve phase matching by compensating for the difference of phase velocity between the fundamental wave and the harmonic wave by means of the double refraction of crystals. However, even when using such crystals which are capable of most efficiently utilizing the $\beta_{333}$ component which is presumably the largest nonlinear polarizability tensor component in terms of molecular level of organic compound, since the directions of the electric field vectors of the fundamental wave and second-harmonic wave are identical to each other, phase matching can hardly be attained.

SUMMARY OF THE INVENTION

One object of the invention is to provide organic nonlinear optical material which shows distinctive nonlinear optical characteristics and which efficiently generates a second harmonic, and which also provides a nonlinear optical element which is capable of efficiently generating a second harmonic by using the above organic nonlinear optical material.

The organic nonlinear optical material according to the invention is substantially composed of a heterocyclic compound represented by formula (I) shown below.

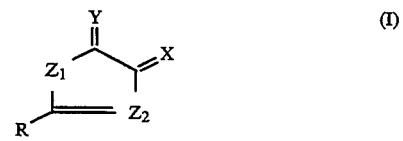

where $Z_1$ is O, S, Se, Te, $SO_2$ group or $NR_1$ group;

$Z_2$ is N or $CR_2$ group;

Y is O, S or $NR_3$ group;

X is $CR_4R_5$ group, $NR_6$ group, O or S; and

R, $R_1$, $R_2$, $R_3$, $R_4$, $R_5$, $R_6$ may be identical to or different from each other, and each of them is a heterocyclic group, an aromatic hydrocarbon group, or an aliphatic hydrocarbon group, which may be unsubstituted or substituted, or a characteristic group or H, where $R_4$ and $R_5$ may jointly form a carbocyclic or a heterocyclic ring.

The nonlinear optical element of the invention is provided with a hollow optical fiber and a single-crystal of the above-mentioned organic nonlinear optical material which fills the hollow space of the optical fiber.

The organic nonlinear optical material of the invention can easily be synthesized, absorbs light having relatively short wavelengths, shows distinctive nonlinear optical characteristics, and efficiently generates a second harmonic. Accordingly, the organic nonlinear optical material of the invention is applicable to not only second harmonic generation but also to optoelectronics utilizing nonlinear phenomena like high-speed light shutters or modulators and optical bistable devices and so on.

The nonlinear optical element according to the invention can easily be manufactured, and generates a second harmonic with high efficiency.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

DETAILED DESCRIPTION OF THE PREFERRED EMBODIMENTS

Figure 1:
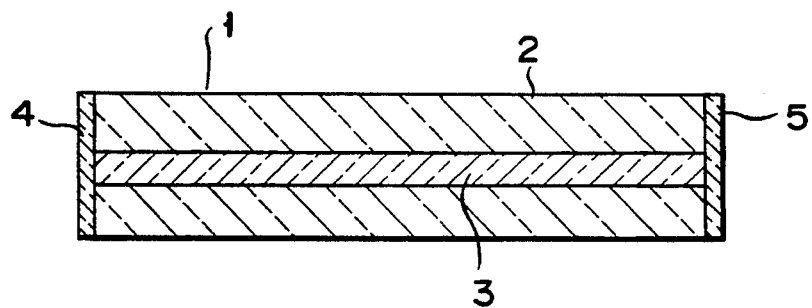
FIG. 1 is the sectional view of the nonlinear optical element according to an example of the invention.

Referring to the foregoing general formula (I), there are a variety of heterocyclic compounds for making up the basic structure by combinations of $Z_1$, $Z_2$, and Y, including the following:

(1) The heterocyclic ketone compounds shown in A to H in Table 1 including 5-oxazolone, 5-thiazolone, 5-imidazolone, 5-thiazolone-1,1-dioxide, 3H-fran-2-one, 3H-thiophen-2-one, 3H-pyrrol-2-one, and 3H-thiapen-2-one-1,1-dioxide.

(2) Those heterocyclic thioketone compound in which O of the carbonyl group of the compounds shown in the above category (1) is substituted with S.

(3) Those heterocyclic Schiff compounds in which O of the carbonyl group of the compounds shown in the above category (1) is substituted with the $NR_3$ group.

Referring to formula (I), examples of unsubstituted heterocyclic groups, aromatic hydrocarbon groups, aliphatic hydrocarbon groups, and alicyclic groups, which are introduced as R, and $R_1$ to $R_6$ are cited below.

Examples of the heterocyclic group are as follows; pyrrole ring, pyrroline ring, pyrrolidine ring, indole ring, isoindole ring, indoline ring, isoindoline ring, indolizine ring, carbazole ring, carboline ring, furan ring, oxolane ring, coumarone ring, coumaran ring, isobenzofuran ring, phthalan ring, dibenzofuran ring, thiophene ring, thiolane ring, benzothiophene ring, dibenzothiophene ring, pyrazole ring, pyrazoline ring, indazole ring, imidazole ring, imidazoline ring, imidazolidine ring, benzimidazole ring, benzimidazoline ring, naphthimidazole ring, oxazole ring, oxazoline ring, oxazolidine ring, benzoxazole ring, benzoxazoline ring, naphthoxazole ring, isoxazole ring, benzisoxazole ring, thiazole ring, thiazoline ring, thiazolidine ring, benzothiazole ring, benzothiazoline ring, naphthothiazole ring, isothiazole ring, benzisothiazole ring, triazole ring, benzotriazole ring, oxadiazole ring, thiadiazole ring, benzoxadiazole ring, benzothiadiazole ring, tetrazole ring, purine ring, pyridine ring, piperidine ring, quinoline ring, isoquinoline ring, acridine ring, phenanthridine ring, benzoquinoline ring, naphthoquinoline ring, naphthyridine ring, phenanthroline ring, pyridazine ring, pyrimidine ring, pyrazine ring, piperazine ring, phthalazine ring, quinoxaline ring, quinazoline ring, cinnoline ring, phenazine ring, perimidine ring, triazine ring, tetrazine ring, pteridine ring, oxazine ring, benzoxazine ring, phenoxazine ring, thiazine ring, benzothiazine ring, phenothiazine ring, oxadiazine ring, thiadiazine ring, dioxolane ring, benzodioxole ring, dioxane ring, benzodioxane ring, dithiolane ring, benzodithiole ring, dithiane ring, benzodithiane ring, pyran ring, chromene ring, xanthene ring, oxane ring, chroman ring, isochroman ring, trioxane ring, thian ring, trithian ring, morpholine ring, quinuclidine ring, selenazole ring, benzoselenazole ring, naphthoselenazole ring, tellurazole ring, benzotellurazole ring, and so on.

Examples of aromatic hydrocarbon group are as follows: phenyl, naphthyl, anthryl, phenanthryl, tetralinyl, azulenyl, biphenylenyl, acenaphthylenyl, acenaphthenyl, fluorenyl, triphenylenyl, pyrenyl, chrysenyl, picenyl, perylenyl, benzopyrenyl, rubicenyl, coronenyl, ovalenyl, indenyl, pentalenyl, heptalenyl, indacenyl, phenalenyl, fluoranthenyl, acephenanthrylenyl, aceanthrenyl, naphthacenyl, pleiadenyl, pentaphenyl, pentacenyl, tetraphenylenyl, hexaphenyl, hexacenyl, trinaphthylenyl, heptaphenyl, heptacenyl, pyranthrenyl, and so on.

Examples of aliphatic hydrocarbon group are as follows: methyl, ethyl, propyl, isopropyl, butyl, isobutyl, sec-butyl, tert-butyl, pentyl, tert-pentyl, isopentyl, neopentyl, hexyl, isohexyl, heptyl, octyl, nonyl, decyl, vinyl, allyl, isopropenyl, propenyl, methallyl, crotyl, ethynyl, propynyl, butenyl, butynyl, pentenyl, pentynyl, butadienyl, and so on.

Examples of alicyclic hydrocarbon group, are as follows: cyclopropyl, cyclobutyl, cyclopentyl, cyclohexyl, cycloheptyl, cyclooctyl, cyclopentenyl, cyclohexenyl, cycloheptenyl, cyclooctenyl, cyclopentadienyl, cyclohexadienyl, and so on.

Referring to the foregoing general formula (I), examples of characteristic group introduced as R, and $R_1$ to $R_6$ are as follows: disubstituted amino group, for example, dimethylamino, diethylamino, dibutylamino, ethylmethylamino, butylmethylamino, diamylamino, dibenzylamino, diphenethylamino, diphenylamino, ditolylamino, dixylylamino, methylphenylamino, and benzylmethylamino; monosubstituted amino group, for example, methylamino, ethylamino, propylamino, isopropylamino, tert-butylamino, anilino, anisidino, phenetidino, toluidino, xylidino, pyridylamino, thiazolylamino, benzylamino, and benzylideneamino; cyclic amino group, for example, pyrrolidino, piperidino, morpholino, 1-pyrrolyl, 1-pyrazolyl, 1-imidazolyl, and 1-triazolyl; acylamino group, for example, formylamino, acetylamino, benzoylamino, cinnamoylamino, pyridinecarbonylamino, and trifluoroacetylamino; amino group; hydroxyamino group; ureido group; semicarbazido group; carbazido group;

disubstituted hydrazino group, for example, dimethylhydrazino, diphenylhydrazino, and methylphenylhydrazino; monosubstituted hydrazino group, for example, methylhydrazino, phenylhydrazino, pyridylhydrazino, and benzylidenehydrazino; hydrazino group; azo group, for example, phenylazo, pyridylazo, and thiazolylazo; azoxy group; amidino group; aminocarbonyl group, for example, carbamoyl, methylcarbamoyl, phenylcarbamoyl, pyridylcarbamoyl, carbazoyl, allophanoyl, oxamoyl, and succinamoyl; cyano group; cyanato group; thiocyanato group; nitro group; nitroso group; oxy group, for example, methoxy, ethoxy, propoxy, butoxy, hydroxyethoxy, phenoxy, naphthoxy, pyridyloxy, thiazolyloxy, and acetoxy; hydroxy group; thio group, for example, methylthio, ethylthio, phenylthio, pyridylthio, and thiazolylthio; mercapto group; halogen group, for example fluoro, chloro, bromo, and iodo; carboxyl group and its salt; oxycarbonyl group, for example, methoxycarbonyl, ethoxycarbonyl, phenoxycarbonyl, and pyridyloxycarbonyl; thiocarboxyl group and its salt; dithiocarboxyl group and its salt; thiocarbonyl group, for example, methoxythiocarbonyl, methylthiocarbonyl, and methylthiothiocarbonyl; acyl group, for example, formyl, acetyl, propionyl, acryloyl, benzoyl, cinnamoyl, pyridinecarbonyl, thiazolecarbonyl, and trifluoroacetyl; thioacyl group, for example, thioformyl, thioacetyl, thiobenzoyl, and pyridinethiocarbonyl; sulfinic acid group and its salt; sulfonic acid and its salt; sulfinyl group, for example, methylsulfinyl, ethylsulfinyl, and phenylsulfinyl; sulfonyl group, for example, methylsulfonyl, ethylsulfonyl, phenylsulfonyl, pyridylsufonyl, tosyl, tauryl, trifluoromethylsulfonyl, sulfamoyl, methylsulfamoyl, sulfanilyl, and acetylsulfanilyl; organosilicic group, for example silyl, disilanyl, trimethylsilyl, and triphenylsilyl; sulfonylamino group, for example, mesylamino, ethylsulfonylamino, phenylsulfonylamino, pyridylsulfonylamino, tosylamino, taurylamino, trifluoromethylsulfonylamino, sulfamoylamino, methylsulfamoylamino, sulfanilylamino, and acetylsulfanilylamino; oxysulfonyl group, for example, methoxysulfonyl, ethoxysulfonyl, phenoxysulfonyl, acetaminophenoxysulfonyl, and pyridyloxysulfonyl; thiosulfonyl group, for example, methylthiosulfonyl, ethylthiosulfonyl, phenylthiosulfonyl, acetaminophenylthiosulfonyl, and pyridylthiosulfonyl; aminosulfonyl group, for example, methylsulfamoyl, dimethylsulfamoyl, ethylsulfamoyl, diethylsulfamoyl, phenylsulfamoyl, acetaminophenylsulfamoyl, and pyridylsulfamoyl; halogenated alkyl group, for example, chloromethyl, bromomethyl, fluoromethyl, dichloromethyl, dibromomethyl, difluoromethyl, trifluoromethyl, pentafluoroethyl, and heptafluoropropyl; and so on.

Referring to formula (I), examples of a carbocyclic and a heterocyclic ring formed jointly by $R_4$ and $R_5$ are as follows: cyclopropane ring, cyclobutane ring, cyclopentane ring, cyclohexane ring, cycloheptane ring, cyclooctane ring, cyclopentene ring, cyclohexene ring, cycloheptene ring, cyclooctene ring, cyclopentadiene ring, cyclohexadiene ring, indan ring, indene ring, tetralin ring, fluorene ring, anthrone ring, oxane ring, thiane ring, piperidine ring, piperazine ring, morpholine ring, oxazoline ring, thiazoline ring, imidazoline ring, isoxazoline ring, isothiazoline ring, pyrazoline ring, benzoxazoline ring, benzothiazoline ring, benzimidazoline ring, benzisoxazoline ring, benzisothiazoline ring, benzothiazoline ring, dihydropyridine ring, dihydroquinoline ring, and so on.

Referring again to formula (I), the above-mentioned heterocyclic, aromatic hydrocarbon, aliphatic hydrocarbon, and alicyclic hydrocarbon entitles, which as cited are unsubstituted, substituted by much groups are, hydrocarbon group for example, alkyl, aryl, alkenyl, and alkynyl, and the heterocyclic groups cited above.

Table 2 R1 through R80 respectively designate examples of the substituent R introduced into formula (I).

Table 3 X1 through X160 respectively designate examples of the substituent X introduced into formula (I).

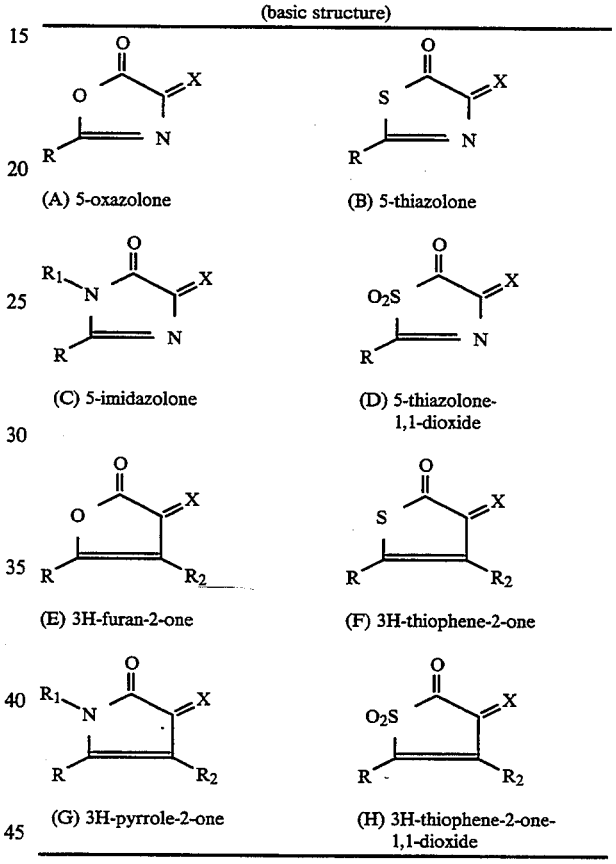

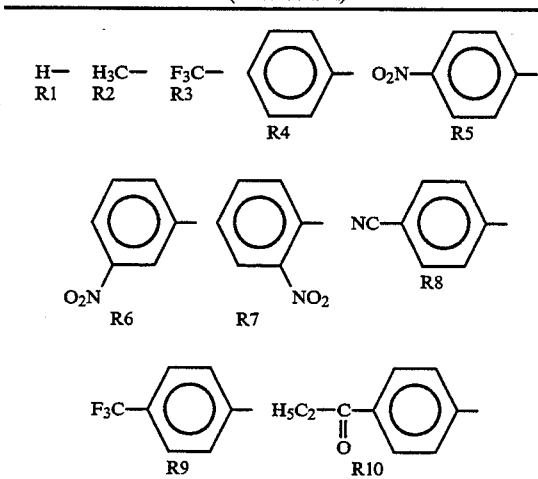

TABLE 2-continued
(substituent R)
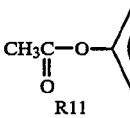 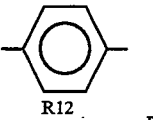 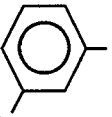
R11     R12     R13
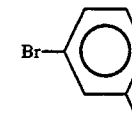 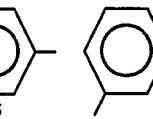 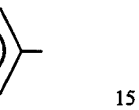
R14     R15     R16
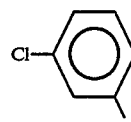 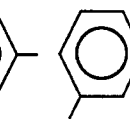 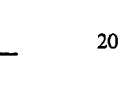
R17     R18     R19
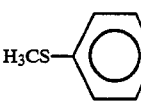 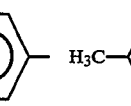 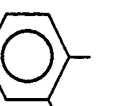
R20     R21     R22
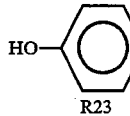 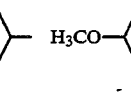 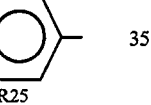
R23     R24     R25
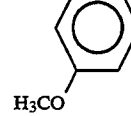 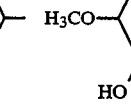 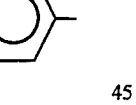
R26     R27     R28
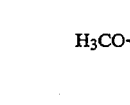 
R29     R30
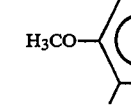 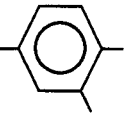
R31     R32
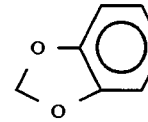 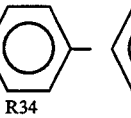 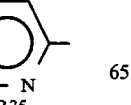
R33     R34     R35
TABLE 2-continued
(substituent R)
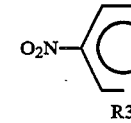 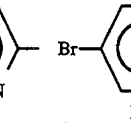 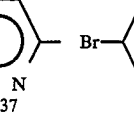
R36     R37     R38
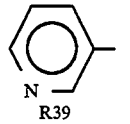 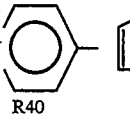 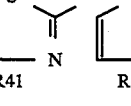 
R39    R40    R41    R42
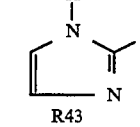 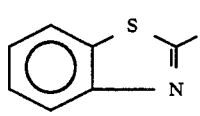
R43     R44
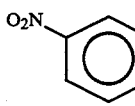 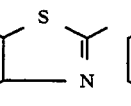
R45     R46
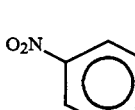 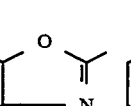
R47     R48
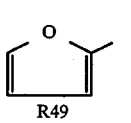 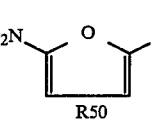 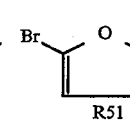
R49     R50     R51
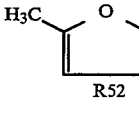 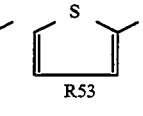 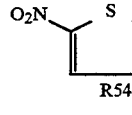
R52     R53     R54
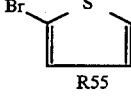 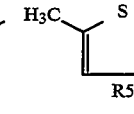 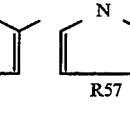
R55     R56     R57
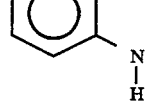 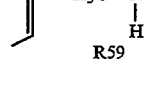 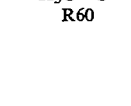
R58     R59     R60
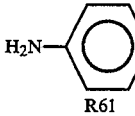 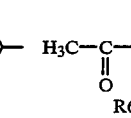
R61     R62

TABLE 2-continued
(substituent R)
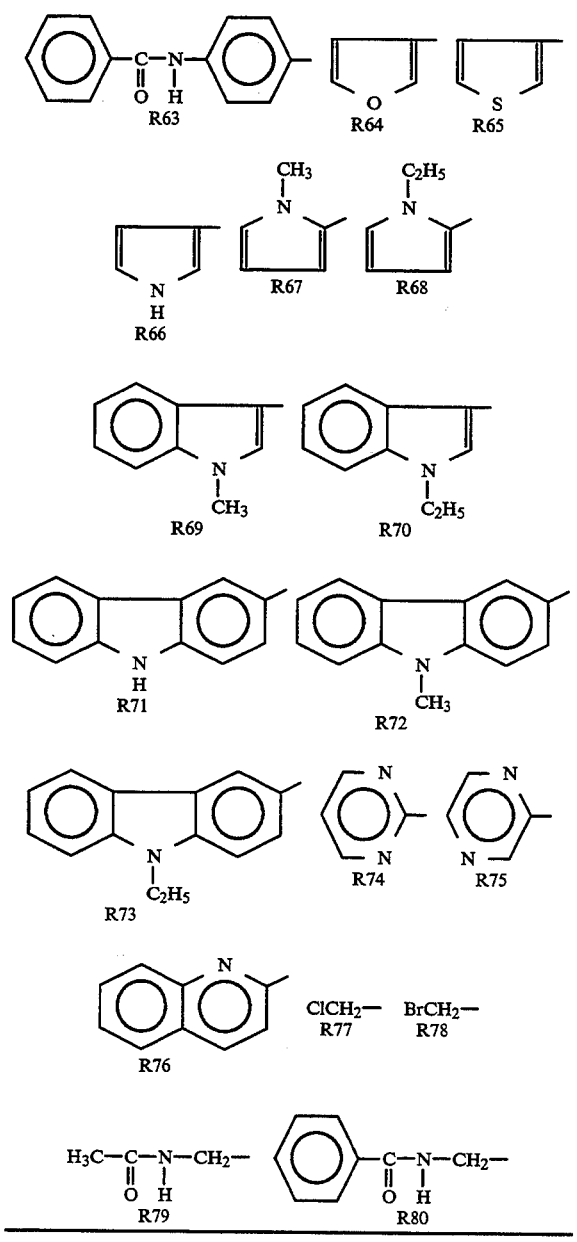
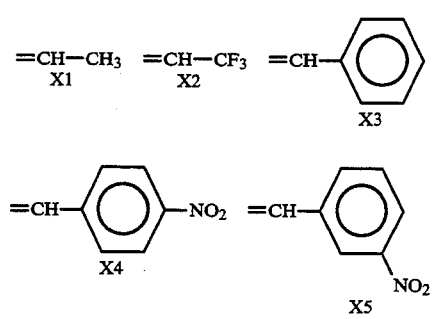
TABLE 3
(substituent X)
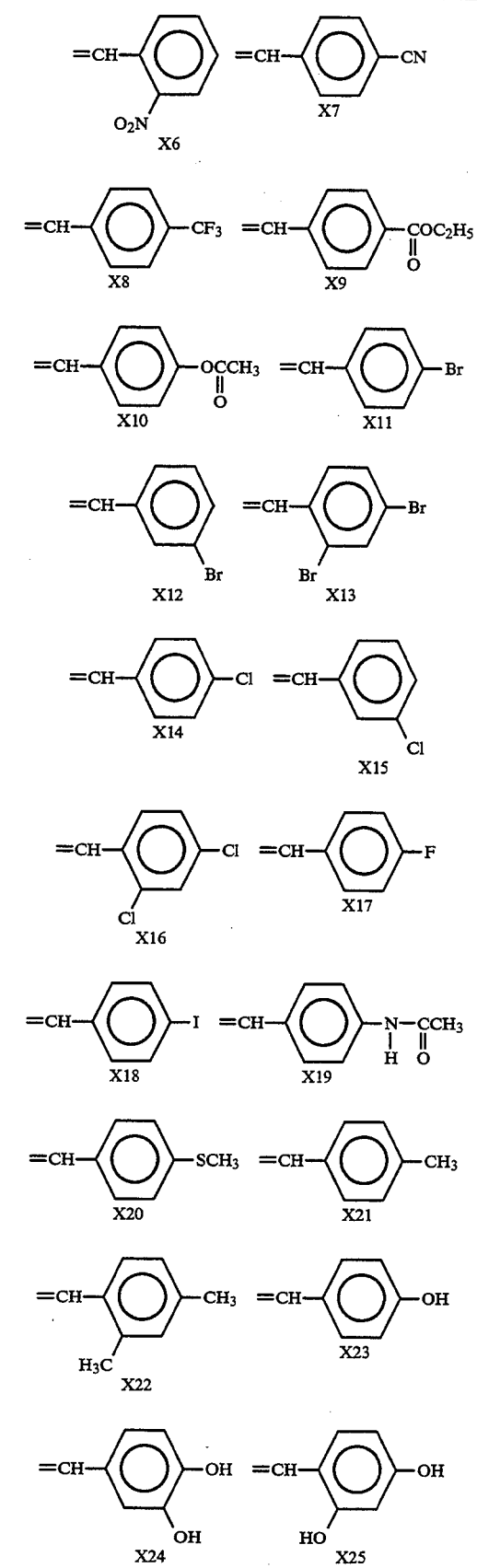

TABLE 3-continued
(substituent X)
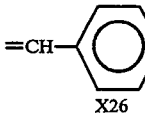
X26
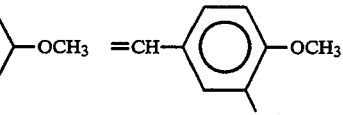
X27
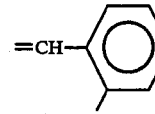
X28
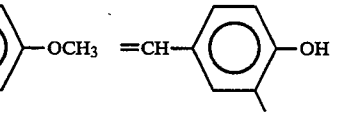
X29
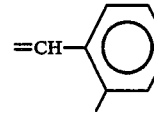
X30
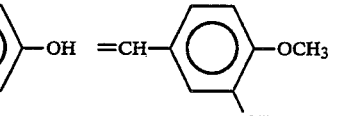
X31
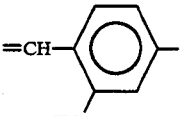
X32
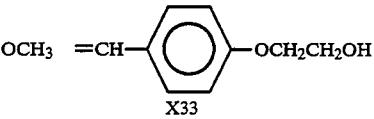
X33
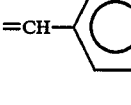
X34
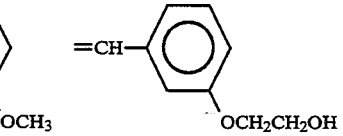
X35
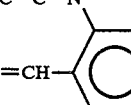
X36
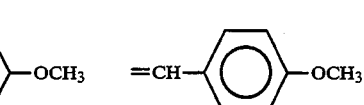
X37
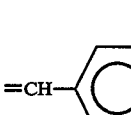
X38
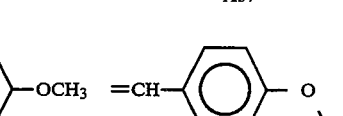
X39
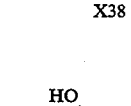
X40
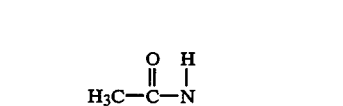
X41
TABLE 3-continued
(substituent X)
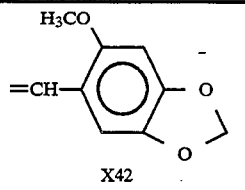
X42
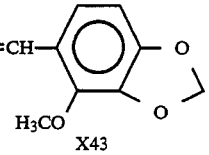
X43
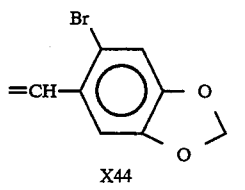
X44
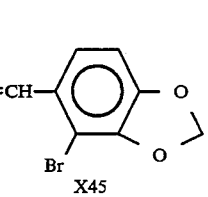
X45
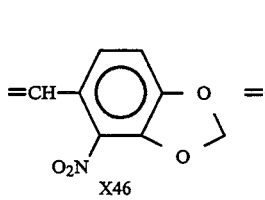
X46
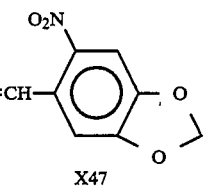
X47
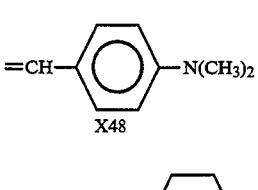
X48
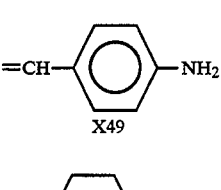
X49
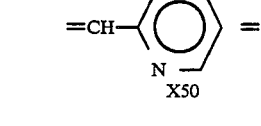
X50
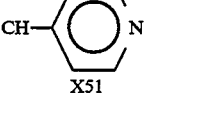
X51
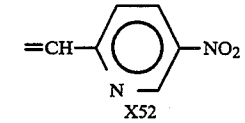
X52
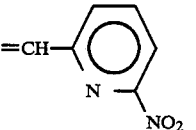
X53
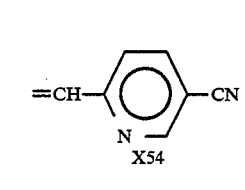
X54
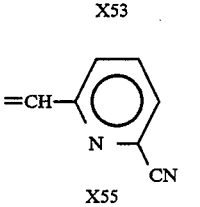
X55
=CH—<pyridine>—CF₃
X56
=CH—<pyridine>
       CF₃
X57
=CH—<pyridine>—C(O)CH₃
X58
=CH—<pyridine>
       CCH₃
       ‖
       O
X59

TABLE 3-continued
(substituent X)
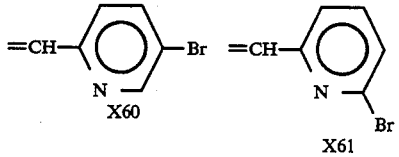

TABLE 3-continued
(substituent X)
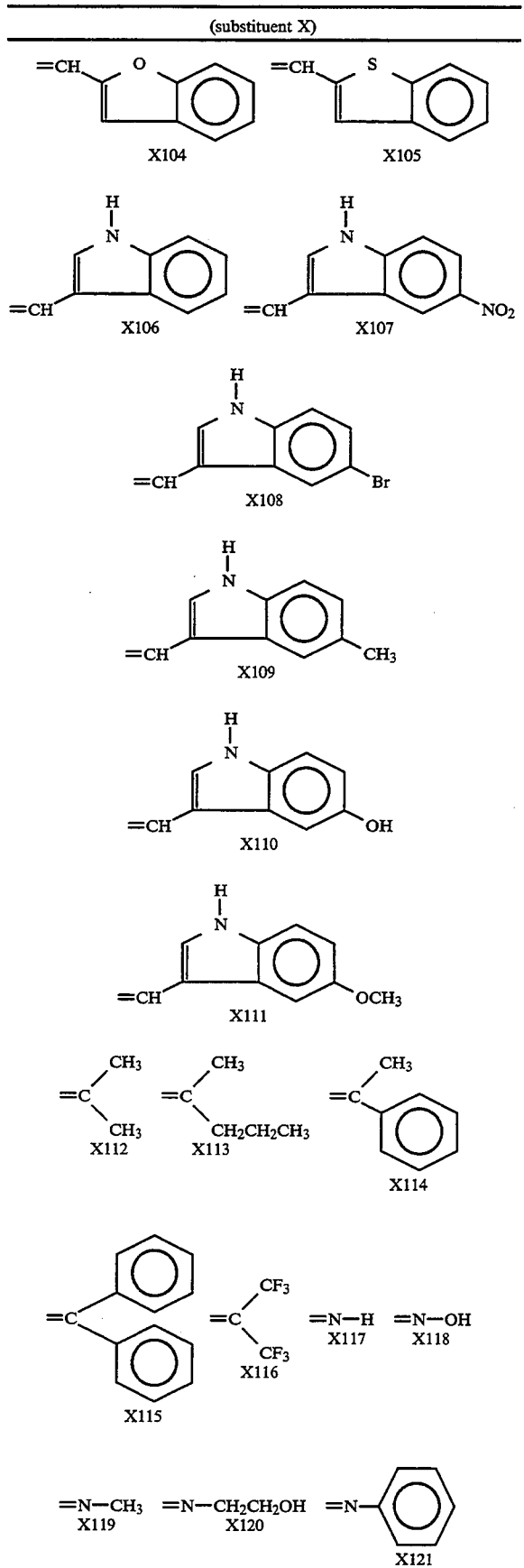
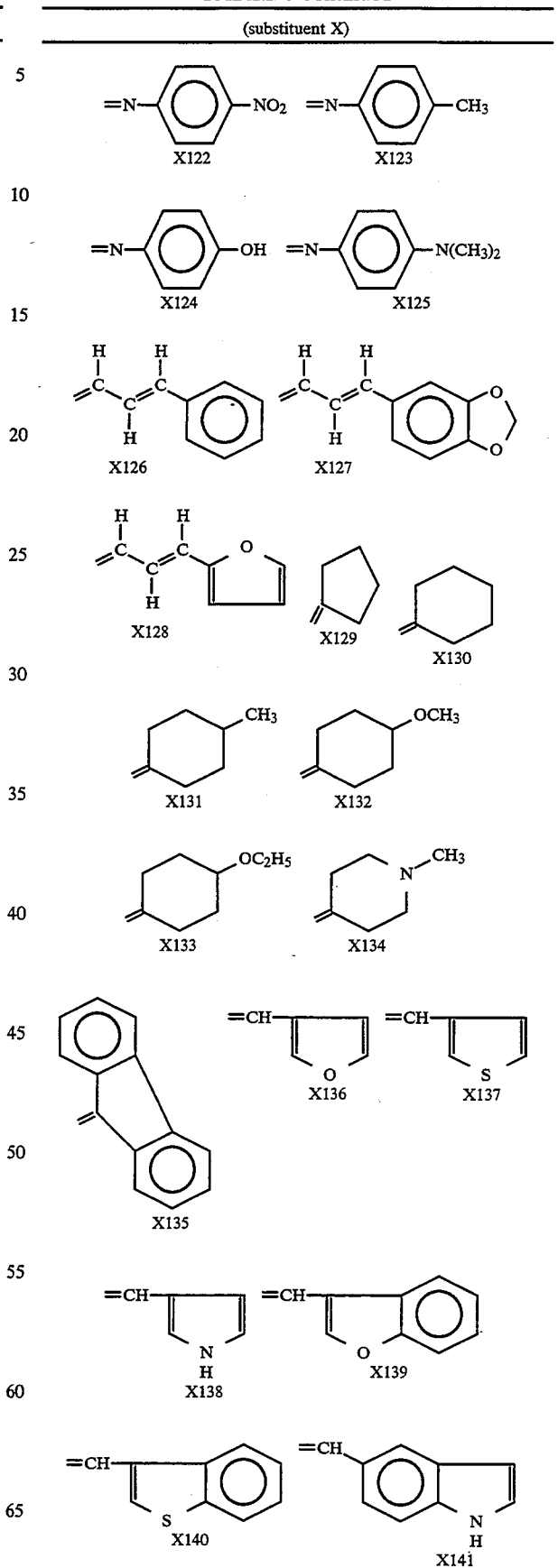

TABLE 3-continued
(substituent X)

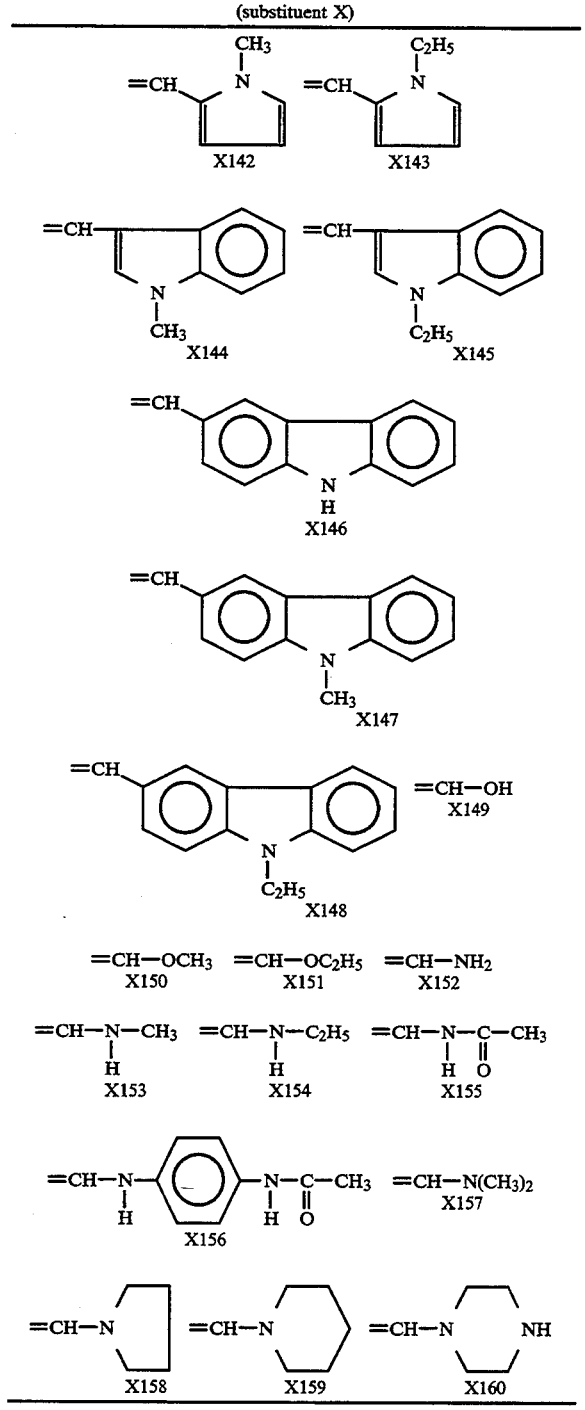

Those compounds represented by the foregoing general formula (I) respectively contain heterocyclic π electrons in the central portion, whereas an electron-withdrawing group and an electron-releasing group are disposed on two sides. As a whole, each of these compounds has a structure which is curved in a characteristic bow shape. Such a compound has substantial nonlinear polarization. However, since the distance between the electron-withdrawing group and the electron-releasing group is short in relation to the length of the bow-string, the dipole moment in the ground state is small. In consequence, any of these compounds cannot easily enter a centrosymmetrical structure in a solid state. This in turn does not inhibit second harmonic generation.

In accordance with the molecular structure of the compound, a variety of characteristics can be generated from the compounds embodied by the invention. For example, consideration is hereby given to such a compound wherein $Z_1$ is O, S or $NR_1$ group; $Z_2$ is N; Y is O; X is $CR_4R_5$ group, where either $R_4$ or $R_5$ is an electron-releasing group; and R is a substantially neutral substituent related to withdrawing and releasing of electrons (neither electron-withdrawing nor electron-releasing). In this case, if an aryl group is selected for R, the intensity of the second harmonic wave is substantially promoted, whereas absorption of the molecule shifts to the longer-wavelength side. On the other hand, if an alkyl group is selected for R, the intensity of the second harmonic wave is not noticeably promoted, and the absorption of the molecule shifts to the shorter-wavelength side.

In the same way, a consideration is also given to another compound wherein; $Z_1$ is O, S, or $NR_1$ group; $Z_2$ is N; Y is O; X is $CR_4R_5$ group, where $R_4$ and $R_5$ are both substantially neutral substituent related to the withdrawing and releasing of electrons; and R is an electron-withdrawing group. In this case, if an aryl group is selected for $R_4$ or $R_5$, the intensity of the second harmonic is substantially promoted, whereas the absorption of molecules shifts to the longer-wavelength side. On the other hand, if an alkyl group is selected for $R_4$ or $R_5$, the intensity of the second harmonic wave is not noticeably promoted, and the absorption of the molecules shifts to the shorter-wavelength side.

Accordingly, it is desired that the molecular structure of compound can be modified in accordance with the needed characteristic when applying the above compounds to a nonlinear optical element.

Generally, the compound expressed by formula (I) can be synthesized by dehydrating and condensing a ketone, thioketone, or ketone-imide, which has an active methylene group, with a carbonyl compound or an isonitroso compound. More particularly, in accordance with the basic structure of the objective compound, a variety of synthesis methods can be available, for example, including the following:

As described by J. S. Buck et al., in Org. Synth., 13, 8 (1933), 5-oxazolone derivative can be synthesized by dehydrating and condensing N-acylglycine and carbonyl compound.

As described by J. B. Jepson et al., in J. Chem. Soc., 1955, 1791 (1955), 5-thiazolone derivative can be synthesized by dehydrating and condensing N-thioacylglycine and carbonyl compound.

As described by H. Lehr et al., in J. Am. Chem. Soc., 75, 3640 (1953), 5-imidazolone derivative can be synthesized by dehydrating and condensing 4,4-dihydro-5-imidazolone compound and carbonyl compound. Likewise, as described by C. Granacher et al., in Helv. Chem. Acta., 10, 819 (1927), 5-imidazolone derivative can also be synthesized by reacting 4-arylidene-5-oxazolone with amino compound.

Also, as described by L. S. El-Assal et al., in J. Chem. Soc., 1961, 1658 (1961), 3H-furan-2-one derivative can be synthesized by dehydrating and condensing β-acylpropionic acid and carbonyl compound.

The nonlinear optical element of the invention can be manufactured by executing those sequential processes described below. First, one end of a hollow optical fiber is immersed in melted organic nonlinear optical material, thereby filling up the hollow space of the fiber with the melt by capillary flow, and then the melt-filled fiber is cooled to solidify the melt. Next, the fiber is heated and gradually cooled to crystallize the organic nonlinear optical material.

The nonlinear optical element of the invention is substantially made of optical fiber which incorporates the organic nonlinear optical material as a core. When operating the nonlinear optical element of the invention, since the Cerenkov phase matching can be attained between the guiding mode of the incident fundamental wave in the core and the radiation mode of the second harmonic from the core to the clad, the nonlinear optical element of the invention can securely generate second-harmonic wave with extremely high efficiency.

Now, based on examples, detail of the invention is described below.

First, examples of synthesis of typical heterocyclic compounds available for the organic nonlinear optical material of the invention are shown below.

Tables 4 to 7 respectively designate the synthesized compounds by combining the following; basic structure which is designated by respective notations (like A, ... , E), R which is designated by abbreviation of substituent and the symbol in Table 2, and X which is designated by a combination of $R_4$ (H-) and abbreviation or name of substituent $R_5$, and the symbol in Table 3.

Synthesis of 5-Oxazolone Derivative 10 ml (106 mmol) of acetic anhydride was added to 33 mmol of N-acylglycine, 30 mmol of aldehyde, and 2.5 g (30 mmol) of sodium acetate anhydride or sodium hydrogen-carbonate anhydride. The mixture was stirred and heated at 100° C. for an hour, and was further stirred at room temperature for 4 to 5 hours. After cooling, the reaction solution was poured into water to precipitate crystals. The precipitated crystals were filtrated and washed with water. The coarse crystals were recrystallized twice from acetic acid, acetone or ethanol, thus the objective compound was obtained. Melting points of respective compounds are shown in Table 4.

Synthesis of 5-Thiazolone Derivative 10 ml (106 mmol) of acetic anhydride was added to 33 mmol of N-thioacylglycine, 30 mmol of aldehyde, and 2.5 g (30 mmol) of sodium acetate anhydride or sodium hydrogencarbonate anhydride. The mixture was stirred and heated at 100° C. for an hour, and was further stirred at room temperature for 4 to 5 hours. After cooling, the reaction solution was poured into water to precipitate crystals. The precipitated crystals were filtrated and washed with water. The coarse crystals were recrystallized twice from acetic acid, acetone or ethanol, thus the objective compound was obtained. Melting points of respective compounds are shown in Table 5.

Synthesis of 5-Imidazolone Derivative (A)

33 mmol of 4,4-dihydro-5-imidazolone compound, 30 mmol of aldehyde, and 1.0 ml (10 mmol) of piperidine were dissolved in 20 ml of toluene or ethanol, and then the mixture was stirred and heated at 70° C. for 5 hours. After cooling, the reaction solution was concentrated under reduced pressure, and then the residue was recrystallized twice from acetic acid, acetone or ethanol, thus the objective compound was obtained.

(B)

20 mmol of 4-arylidene-5-oxazolone derivative was dissolved in 50 ml of ethanol, and then 100 mmol of amino compound was added to the mixture. The mixture was refluxed for an hour. The reaction solution was cooled to precipitate crystals. The precipitated coarse crystals were filtrated and washed with water. The coarse crystals were recrystallized from ethanol, thus $\beta$-aryl-$\alpha$-(N-acylamino) acrylamide derivative was obtained. The derivative was heated at 170° C. to 180° C. under reduced pressure, and cooled to precipitate crystals. The coarse crystals were recrystallized twice from acetic acid, acetone or ethanol, thus the objective compound was obtained.

Melting points of respective compounds are shown in Table 6.

Synthesis of 3H-Furan-2-One Derivative 10 ml (106 mmol) of acetic anhydride was added to 33 mmol of $\beta$-acylpropionic acid, 30 mmol of aldehyde, and 2.5 g (30 mmol) of sodium acetate anhydride or sodium hydrogencarbonate anhydride. The mixture was stirred and heated at 100° C. for an hour, and was further stirred at room temperature for 4 to 5 hours. After cooling, the reaction solution was poured into water to precipitate crystals. The precipitated crystals were filtrated and washed with water. The coarse crystals were recrystallized twice from acetic acid, acetone or ethanol, thus the objective compound was obtained. Melting points of respective compounds are shown in Table 7.

Examples 1 to 20

With respect to the obtained 5-oxazolone derivatives, 5-thiazolone derivatives, 5-imidazolone derivatives, and 3H-furan-2-one derivatives, the second-order nonlinear optical characteristic was evaluated by powder method, as follows. Crystal powder of respective compounds was ground with an agate mortar. Each powder was sieved to adjust particle size to a range from 100 to 150 microns. Each powder was sandwitched between a couple of glass slides, thus samples for measurement were prepared. Then, the fundamental wave (having 1.064 μm of wave length) of an Nd-YAG laser was irradiated against each sample, and the intensity of second harmonic (SH) light in reflective light was measured. High-purity urea powder was used as the reference sample. SH intensity of respective samples was normalized with SH intensity of urea powder. Results of the measurement are shown in Table 8. Table 8 also designates the maximum absorption wavelength in visible-ultraviolet spectrum.

TABLE 4

| No. | Basic Structure Symbol | R | R Symbol | X $R_4$ | X $R_5$ | X Symbol | Melting Point (°C.) |
|---|---|---|---|---|---|---|---|
| A1 | A | Me— | R2 | H— | 3,4-OCH$_2$O—Ph— | X39 | 181 |
| A2 |   | Ph— | R4 | H— | Ph— | X3 | 166 |

TABLE 4-continued

| No. | Basic Structure Symbol | R | | X | | | Melting Point (°C.) |
|---|---|---|---|---|---|---|---|
| | | R | Symbol | R4 | R5 | Symbol | |
| A3 | | Ph— | R4 | H— | 3,4-OCH2O—Ph— | X39 | 197 |
| A4 | | Ph— | R4 | H— | 4-Me2NPh— | X48 | 214 |
| A5 | | Ph— | R4 | H— | 3-indolyl- | X106 | 221 |
| A6 | | 4-NO2Ph— | R5 | H— | 4-MeOPh— | X26 | 250 |
| A7 | | 4-NO2Ph— | R5 | H— | 3,4-(MeO)2Ph— | X27 | 267 |
| A8 | | 4-NO2Ph— | R5 | H— | 3,4-OCH2O—Ph— | X39 | 245 |
| A9 | | 4-NO2Ph— | R5 | H— | 2-furyl- | X85 | 248 |
| A10 | | 3-NO2Ph— | R6 | H— | 4-MeOPh— | X26 | 214 |
| A11 | | 3-NO2Ph— | R6 | H— | 3,4-OCH2O—Ph— | X39 | 196 |
| A12 | | 4-BrPh— | R12 | H— | 2-furyl- | X85 | 202 |
| A13 | | 4-ClPh— | R15 | H— | Ph— | X3 | 179 |
| A14 | | 2-NO2Ph— | R7 | H— | Ph— | X3 | 148 |
| A15 | | 4-NO2Ph— | R5 | H— | Ph— | X3 | 229 |

TABLE 5

| No. | Basic Structure Symbol | R | | X | | | Melting Point (°C.) |
|---|---|---|---|---|---|---|---|
| | | R | Symbol | R4 | R5 | Symbol | |
| B1 | B | Me— | R2 | H— | Ph— | X3 | 130 |
| B2 | | Ph— | R4 | H— | Ph— | X3 | 132 |
| B3 | | Ph— | R4 | H— | 4-MePh— | X21 | 121 |
| B4 | | Ph— | R4 | H— | 4-MeOPh— | X26 | 159 |
| B5 | | MeS— | R60 | H— | Ph— | X3 | 98 |
| B6 | | MeS— | R60 | H— | 4-NO2Ph— | X4 | 215 |
| B7 | | MeS— | R60 | H— | 4-ClPh— | X14 | 146 |
| B8 | | MeS— | R60 | H— | 4-MePh— | X21 | 124 |
| B9 | | MeS— | R60 | H— | 4-MeOPh— | X26 | 159 |
| B10 | | MeS— | R60 | H— | 2-furyl- | X85 | 74 |

TABLE 8

| | Compound No. | Max. Absorption Wavelength (nm in toluene) | Intensity of SH (Ratio vs urea) |
|---|---|---|---|
| Example 1 | A1 | 363 | 15 |
| Example 2 | A2 | 386, 366 | 3 |
| Example 3 | A3 | 416, 396 | 22 |
| Example 4 | A15 | 400 | 30 |
| Example 5 | A5 | 426 | 30 |
| Example 6 | A6 | 417 | 2 |
| Example 7 | A11 | 404 | 18 |
| Example 8 | B2 | 380 | 4 |
| Example 9 | B4 | 400 | 13 |
| Example 10 | B5 | 372 | 1 |
| Example 11 | B9 | 392 | 11 |
| Example 12 | C5 | 370 | 2 |
| Example 13 | C6 | 400 | 14 |
| Example 14 | C9 | 401 | 10 |
| Example 15 | C12 | 362 | 1 |
| Example 16 | E1 | 384 | 1 |
| Example 17 | E3 | 385 | 1 |
| Example 18 | E5 | 402 | 10 |

TABLE 6

| No. | Basic Structure Symbol | R | | | X | | | Melting Point (°C.) |
|---|---|---|---|---|---|---|---|---|
| | | R1 | R | Symbol | R4 | R5 | Symbol | |
| C1 | C | Ph— | Ph— | R4 | H— | Ph— | X3 | 180 |
| C2 | | H— | Ph— | R4 | H— | 3-NO2Ph— | X5 | 295 |
| C3 | | HO— | Ph— | R4 | H— | 3-NO2Ph— | X5 | 198 |
| C4 | | HO— | Ph— | R4 | H— | 4-BrPh— | X11 | 257 |
| C5 | | H— | Ph— | R4 | H— | 4-ClPh— | X14 | 306 |
| C6 | | H— | Ph— | R4 | H— | 3,4-(MeO)2Ph— | X27 | 261 |
| C7 | | H— | 4-NO2Ph— | R5 | Me— | Me— | X112 | 259 |
| C8 | | H— | 4-ClPh— | R15 | H— | Ph— | X3 | 332 |
| C9 | | Me— | 4-MeOPh— | R25 | H— | Ph— | X3 | 163 |
| C10 | | H— | 4-MeOPh— | R25 | Me— | CH3CH2CH2— | X113 | 176 |
| C11 | | H— | 4-MeOPh— | R25 | | 4-methoxy-cyclohexyl- | X132 | 196 |
| C12 | | H— | MeS— | R60 | H— | Ph— | X3 | 150 |
| C13 | | Ph— | MeS— | R60 | H— | Ph— | X3 | 151 |

TABLE 7

| No. | Basic Structure Symbol | R | | X | | | Melting Point (°C.) |
|---|---|---|---|---|---|---|---|
| | | R2 | R | Symbol | R4 | R5 | Symbol | |
| E1 | E | H— | Ph— | R4 | H— | Ph— | X3 | 150 |
| E2 | | H— | Ph— | R4 | H— | 4-NO2Ph— | X4 | 293 |
| E3 | | H— | Ph— | R4 | H— | 3-NO2Ph— | X5 | 205 |
| E4 | | H— | Ph— | R4 | H— | 4-ClPh— | X14 | 229 |
| E5 | | H— | Ph— | R4 | H— | 4-MeOPh— | X26 | 171 |
| E6 | | H— | Ph— | R4 | H— | 3,4-OCH2O—Ph— | X39 | 229 |
| E7 | | H— | Ph— | R4 | H— | 4-Me2NPh— | X48 | 175 |
| E8 | | H— | 4-ClPh— | R15 | H— | 3-MeOPh— | X34 | 172 |
| E9 | | H— | 4-MePh— | R21 | H— | Ph— | X3 | 177 |
| E10 | | H— | 4-MePh— | R21 | H— | 3,4-OCH2O—Ph— | X39 | 215 |

TABLE 8-continued

| | Compound No. | Max. Absorption Wavelength (nm in toluene) | Intensity of SH (Ratio vs urea) |
|---|---|---|---|
| Example 19 | E6 | 408 | 18 |
| Example 20 | E10 | 416 | 15 |

Examples 21 to 25

An example of the optical-fiber type nonlinear optical element of the present invention is described below. FIG. 1 is the sectional view of the nonlinear optical element. The nonlinear optical element 1 comprises clad 2 composed of a quartz-made hollow fiber having 100 μm of external diameter, 2 μm of internal diameter, and 100 mm of length, and core 3 made of singlecrystal of the compound represented by the foregoing general formula (I). A reflection preventive film 4 against incident fundamental wave is formed on the surface of one end of the nonlinear optical element 1, whereas a reflection preventive film 5 against the generated second-harmonic wave is formed on the surface of the other end.

The nonlinear optical element having the above-mentioned structure was manufactured in accordance with sequential processes described below. Those compounds (shown in Table 9 by numbers in Tables 4 to 7) represented by the foregoing general formula (I) were melted, and held at such temperature 10° C. higher than the melting points of respective compounds. One end of the quartz-made hollow fiber was immersed in each melt, thereby filling up the hollow space with the melt availing of capillarity. The melt-filled fiber was removed from the melt, and then quickly cooled to solidify the melt filled in the hollow space. At this point, the compounds were in a state of fine crystals. In order to prevent these compounds from being oxidized, these processes were executed in a nitrogen glove box.

Each fiber filled with fine crystals in its hollow space was conveyed in a furnace held at temperature 10° C. higher than the melting point of each compound, and then gradually extracted from the furnace. The compound was crystallized at the extracted portion, and as a result, singlecrystal of each compound grew up in the hollow space of the fiber. Optimal rate of extracting the fiber from the furnace is variable corresponding to the kind of the compounds. Therefore, the optimal extracting rate was preliminarily determined, by observing quality of crystals formed under various extracting rate with a polarized microscope. In order to prevent the compounds from being oxidized, the process for growing the crystals was also carried out in a nitrogen glove box.

The end portions of the produced elements were cut off and then polished. The reflection preventive film 4 against the incident fundamental wave on the surface of one end, and the reflection preventive film 5 against the generated second-harmonic wave on the surface of the other end were formed by sputtering $MgF_2$ for each element.

Figure 2:
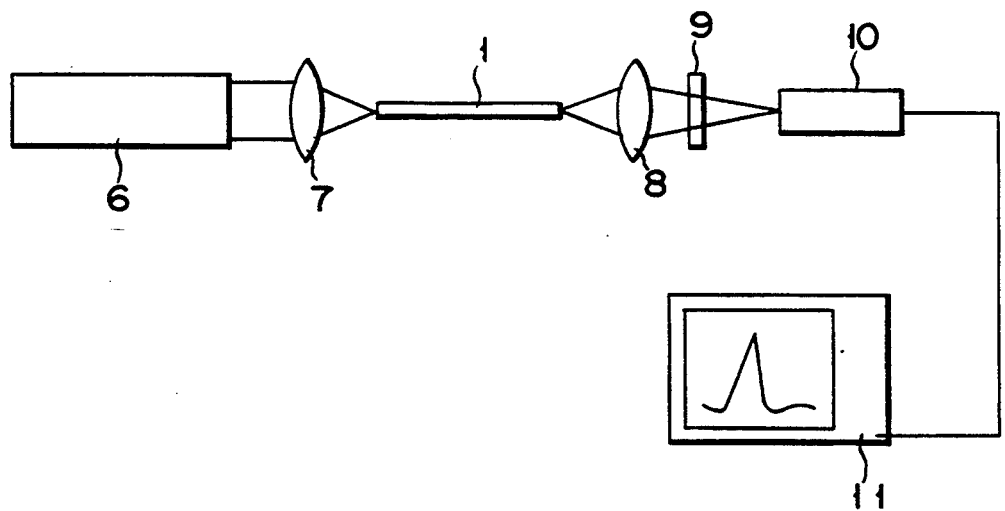
FIG. 2 is a simplified diagram of an apparatus for measuring the efficiency of second harmonic generation by the nonlinear optical element according to an example of the invention.

In order to evaluate performance of the produced optical fiber-type nonlinear optical elements, SHG efficiency was measured using the fundamental wave (having 1.064 μm of wavelength) from an Nd-YAG laser, as shown in FIG. 2.

Laser beam from the Nd-YAG laser 6 was irradiated through a lens 7, of which numerical aperture (NA) is 0.5, onto the core 3 at one end of the element. The intensity of the incident basic wave was 10 nJ/pulse, the pulse width was 10 ns, and the pulse repetition frequency was 10 Hz, respectively. The generated second-harmonic wave was allowed to pass through a lens 8 and an interference filter 9 set to 532 nm corresponding to the wavelength of the second harmonic wave, thereby being converged to a photoelectron multiplier 10, and the intensity of SH light was measured by operating a digital oscilloscope 11. Since the second-harmonic wave from the fiber formed ring-shaped pattern, it was confirmed that the Cerenkov radiation type phase matching was attained.

Table 9 shows the SHG efficiency of each element. As is clear from Table 9, each element yielded 40 to 50% of the conversion efficiency against 10 nJ of input pulse. It is estimated from these results that substantial amount of the second-harmonic wave enough for practical use can be generated even when semiconductor lasers, having about 100 mW of output, are used.

TABLE 9

| | Compound No. | SHG Efficiency (%) |
|---|---|---|
| Example 21 | A1 | 48 |
| Example 22 | A11 | 51 |
| Example 23 | B4 | 41 |
| Example 24 | C12 | 39 |
| Example 25 | E3 | 47 |

Additional advantages and modifications will readily occur to those skilled in the art. Therefore, the invention in its broader aspects is not limited to the specific details, and representative devices, shown and described. Accordingly, various modifications may be made without departing from the spirit or scope of the general inventive concept as defined by the appended claims and their equivalents.

What is claimed is:

1. A method of obtaining a nonlinear optical effect by irradiating an organic nonlinear optical material with light, wherein said organic nonlinear optical material consists of a heterocyclic compound of the formula:

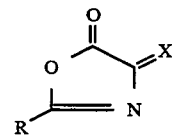

wherein X is $CR_4R_5$, $NR_6$, O or S; and R, $R_4$, $R_5$ and $R_6$ may be identical to or different from each other, and each is a heterocyclic group, an aromatic hydrocarbon group, an aliphatic hydrocarbon group or an alicyclic hydrocarbon group, which may be unsubstituted or substituted, a characteristic group, or H, or $R_4$ and $R_5$ may jointly form a carbocyclic or a heterocyclic ring.

2. The method according to claim 1, wherein said characteristic group is at least one group selected from the group consisting of disubstituted amino group, monosubstituted amino group, cyclic amino group, acyl amino group, amino group, hydroxyamino group, ureido group, semicarbazido group, carbazido group, disubstituted hydrazino group, monosubstituted hydrazino group, hydrazino group, azo group, azoxy group, amidino group, aminocarbonyl group, cyano group, cyanato group, thiocyanato group, nitro group, nitroso group, oxy group, hydroxy group, thio group, mercapto group, halogen group, carboxyl group and its salt, oxycarbonyl group, thiocarboxyl group and its salt, dithiocarboxyl group and its salt, thiocarbonyl group, acyl group, thioacyl group, sulfinic acid group and its salt, sulfonic acid group and its salt, sulfinyl group, sulfonyl group, organosilicic group, sulfonylamino group, oxysulfonyl group, thiosulfonyl group, amino sulfonyl group, and halogenated alkyl group.

3. The method according to claim 1, wherein X is CR$_4$R$_5$; either R$_4$ or R$_5$ is an electron-releasing substituent; and R is substantially a neutral substituent exhibiting an electron withdrawing or releasing effect.

4. The method according to claim 3, wherein R is aryl.

5. The method according to claim 3, wherein R is alkyl.

6. The method according to claim 3, wherein
(1) said electron-releasing substituent is a group selected from the group consisting of (a) a heterocyclic ring, which may be unsubstituted or substituted, and (b) an aromatic hydrocarbon or a heterocyclic ring substituted by an electron-releasing substituent, said electron-releasing substituent being selected from the group consisting of disubstituted amino group, monosubstituted amino group, cyclic amino group, acyl amino group, sulfonyl amino group, amino group, hydroxyamino group, ureido group, semicarbazido group, carbazido group, disubstituted hydrazino group, monosubstituted hydrazino group, hydrazino group, azoxy group, amidino group, oxy group, hydroxy group, thio group, mercapto group and its salt, and organosilicic group; said heterocyclic ring (a) being selected from pyrrole ring, pylloline ring, pyllolidine ring, indole ring, isoindole ring, indoline ring, isoindoline ring, indolizine ring, carbazole ring, furan ring, oxolane ring, coumarone ring, coumaran ring, isobenzofuran ring, phthalan ring, dibenzofuran ring, thiophene ring, thiolane ring, benzothiophene ring, dibenzothiophene ring, pyrazole ring, pyrazoline ring, indazole ring, imidazole ring, imidazoline ring, imidazolidine ring, benzimidazole ring, benzimidazoline ring, naphthimidazole ring, oxazoline ring, oxazolidine ring, benzoxazoline ring, thiazoline ring, thiazolidine ring, benzothiazoline ring, triazole ring, benzotriazole ring, tetrazole ring, piperidine ring, piperadine ring, oxazine ring, benzoxazine ring, phenoxazine ring, thiazine ring, benzothiaine ring, phenothiazine ring, oxadiazine ring, thiadiazine ring, dioxolane ring, benzodioxole ring, dioxane ring, benzodioxane ring, dithiolane ring, benzodithiole ring, dithiane ring, benzodithiane ring, pyran ring, chromene ring, xanthene ring, oxane ring, chroman ring, isochroman ring, trioxane ring, thiane ring, trithiane ring, morpholine ring, and quinuclidine ring; and
(2) said neutral group is selected from the group consisting of unsubstituted aromatic hydrocarbon, unsubstituted aliphatic hydrocarbon and hydrogen.

7. The method according to claim 1, wherein X is CR$_4$R$_5$; both R$_4$ and R$_5$ are substantially neutral substituents having an election withdrawing or releasing effect; and R is an electron-withdrawing substituent.

8. The method according to claim 7, wherein
(1) said electron-withdrawing substituent is a group selected from the group consisting of (a) heterocyclic ring, which may be unsubstituted or substituted, and (b) an aromatic hydrocarbon or a heterocyclic ring substituted by an electron-withdrawing substituent, said electron-withdrawing substituent being selected from the group consisting of nitro group, nitroso group, cyano group, cyanato group, thiocyanato groups, halogen group, carboxyl group and its salt, oxycarbonyl group, aminocarbonyl group, thiocarboxyl group and its salt, dithiocarboxyl group and its salt, thiocarbonyl group, acyl group, thioacyl group, sulfinic acid group and its salt, sulfonic acid group and its salt, sulfinyl group, sulfonyl group, oxysulfonyl group, thiosulfonyl group, amino sulfonyl group, halogenated alkyl group, and azo group; said heterocyclic ring (a) being selected from oxazole ring, benzoxazole ring, naphthoxazole ring, isoxazole ring, benzisoxazole ring, thiazole ring, benzothiazole ring, naphthothiazole ring, isothiazole ring, benzisothiazole ring, oxadiazole ring, thiadiazole ring, benzoxadiazole ring, benzothiadiazole ring, pyridine ring, quinoline ring, isoquinoline ring, acridine ring, phenanthridine ring, benzoquinoline ring, naphthoquinoline ring, naphthyridine ring, phenanthroline ring, pyridazine ring, pyrimidine ring, pyrazine ring, phthalazine ring, quinoxaline ring, quinazoline ring, cinnoline ring, phenazine ring, triazine ring, tetrazine ring, pteridine ring, selenazole ring, and benzoselenazole ring; and
(2) said neutral substituent is selected from the group consisting of unsubstituted aromatic hydrocarbon, unsubstituted aliphatic hydrocarbon and hydrogen.

9. The method according to claim 7, wherein R$_4$ and R$_5$ are aryl or H.

10. The method according to claim 7, wherein R$_4$ and R$_5$ are alkyl or H.

11. The method according to claim 1, wherein said heterocyclic compound has the following chemical structure:

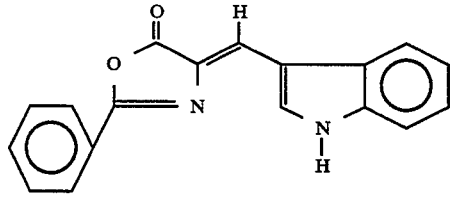

12. The method according to claim 1, wherein said heterocyclic group in a member selected from the group of ring systems consisting of pyrrole, pyrroline, pyrrolidine, indole, isoindole, indoline, isoindoline, indolizine, carbazole, carboline, furan, oxolane, coumarone, coumaran, isobenzofuran, phthalan, dibenzofuran, thiophene, thiolane, benzothiophene, dibenzothiophene, pyrazole, pyrazoline, indazole, imidazole, imidazoline, imidazolidine, benzimidazole, benzimidazoline, naphthimidazole, oxazole, oxazoline, oxazolidine, benzoxazole, benzoxazoline, naphthoxazole, isoxazole, benzisoxazole, thiazole, thiazoline, thiazolidine, benzothiazole, benzothiazoline, naphthothiazole, isothiazole, benzisothiazole, triazole, benzotriazole, oxadiazole, thiadiazole, benzoxadiazole, benzothiadiazole, tetrazole, purine, pyridine, piperidine, quinoline, isoquinoline, acridine, phenanthridine, benzoquinoline, naphthoquinoline, naphthyridine, phenanthroline, pyridazine, pyrimidine, pyrazine, piperazine, phthalazine, quinoxaline, quinazoline, cinnoline, phenazine, perimidine, triazine, tetrazine, pteridine, oxazine, benzoxazine, phenoxazine, thiazine, benzothiazine, phenothiazine, oxadiazine, thiadiazine, dioxolane, benzodioxole, dioxane, benzodioxane, dithiolane, benzodithiole, dithiane, benzodithiane, pyran, chromene, xanthene, oxane, chroman, isochroman, trioxane, thian, trithian, morpholine, quinuclidine, selenazole, benzoselenazole, naphthoselenazole, tellurazole and benzotellurazole.

13. The method according to claim 1, wherein said aromatic hydrocarbon group is a member selected from the group consisting of phenyl, naphthyl, anthryl, phenanthryl, tetralinyl, azulenyl, biphenylenyl, acenaphthylenyl, acenaphthenyl, fluorenyl, triphenylenyl, pyrenyl, chrysenyl, picenyl, perylenyl, benzopyrenyl, rubicenyl, coronenyl, ovalenyl, indenyl, pentalenyl, heptalenyl, indacenyl, phenalenyl, fluoranthenyl, acephenanthrylenyl, aceanthrenyl, naphthacenyl, pleiadenyl, pentaphenyl, pentacenyl, tetraphenylenyl, hexaphenyl, hexacenyl, trinaphthylenyl, heptaphenyl, heptacenyl and pyranthrenyl.

14. The method according to claim 1, wherein said aliphatic hydrocarbon group is a member selected from the group consisting of methyl, ethyl, propyl, isopropyl, butyl, isobutyl, sec-butyl, tert-butyl, pentyl, tert-pentyl, isopentyl, neopentyl, hexyl, isohexyl, heptyl, octyl, nonyl, decyl, vinyl, allyl, isopropenyl, propenyl, methallyl, crotyl, ethynyl, propynyl, butenyl, butynyl, pentenyl, pentynyl and butadienyl.

15. The method according to claim 1, wherein said alicyclic hydrocarbon group is a member selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, cyclopentadienyl and cyclohexadienyl.

* * * * *